US006326365B1

(12) United States Patent
Simpkins et al.

(10) Patent No.: US 6,326,365 B1
(45) Date of Patent: Dec. 4, 2001

(54) METHODS OF PREVENTION AND TREATMENT OF ISCHEMIC DAMAGE

(75) Inventors: James W. Simpkins, Gainsville, FL (US); Katherine D. Gordon, Winchester; Robert J. Leonard, Wellesley, both of MA (US)

(73) Assignees: Apollo BioPharmaceutics, Inc., Cambridge, MA (US); University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 09/358,182

(22) Filed: Jul. 20, 1999

(51) Int. Cl.$^7$ ................................................ A61K 31/56

(52) U.S. Cl. .......................... 514/179; 514/180; 514/181

(58) Field of Search .................................. 514/179, 180, 514/181

(56) References Cited

U.S. PATENT DOCUMENTS

| | | | |
|---|---|---|---|
| 4,897,389 | 1/1990 | Aroonsakul | 514/171 |
| 5,393,763 | 2/1995 | Black | 514/333 |
| 5,512,557 | 4/1996 | Collins | 514/182 |
| 5,550,029 | 8/1996 | Simpkins et al. | 435/14 |
| 5,554,601 | 9/1996 | Simpkins et al. | 514/182 |
| 5,641,790 | 6/1997 | Draper | 514/333 |
| 5,686,476 | 11/1997 | May | 514/324 |
| 5,824,672 | 10/1998 | Simpkins et al. | 514/182 |
| 5,843,934 | 12/1998 | Simpkins | 514/182 |
| 5,859,001 | 1/1999 | Simpkins et al. | 514/182 |
| 5,877,169 | 3/1999 | Simpkins | 517/179 |
| 5,972,923 | 10/1999 | Simpkins et al. | 514/182 |
| 6,197,833 | 3/2001 | Simpkins et al. | 514/730 |
| 6,207,658 | 3/2001 | Simpkins et al. | 514/182 |

FOREIGN PATENT DOCUMENTS

| | | |
|---|---|---|
| 0 753 300 A1 | 6/1996 | (EP) . |
| WO 92/13538 | 8/1992 | (WO) . |
| WO 92/14474 | 9/1992 | (WO) . |
| WO 94/28905 | 12/1994 | (WO) . |
| WO 95/13076 | 5/1995 | (WO) . |
| WO 95/12402 | 11/1995 | (WO) . |

OTHER PUBLICATIONS

Wroblewski et al., *Proc. Soc. Exp. Biol. Med.* 90:210–213, 1955.
Black et al., *Exp. Cell Research* 35:9–13, 1964.
Oldendorf, *Brain Res.* 24:37–46, 1970.
Oldendorf, *Am. J. Physiol.* 221:1629=1638, 1971.
Fonnum, *J. Neurochem.* 24:407–409, 1975.
Kolbe et al., *Biochemistry & Biophysics* 73:378–382, 1976.
Keller et al., *Archives of Pharmacology* 294:213–215, 1976.
Perez–Polo et al., *Life Sci.* 21:1535–1543, 1977.
Luine et al., *Brain Research* 191:273–277, 1980.
Barde et al., *EMBO J.* 1:549–553, 1982.
Fallon et al., *Science* 224:1107–1109, 1984.
Morrison et al., *Prc. Nat'l. Acad. Sci. U.S.A.* 83:7537–7541, 1986.
Morse et al., *Experimental Neurology* 94:649–658, 1986.
Aizeman et al., *Proc. Nat'l. Acad. Sci. U.S.A.* 83:2263–2266, 1986.
Fillet et al., *Psychoneuroendocrinology* 11:337–345, 1986.
Morrison et al., *Science* 238:72–75, 1987.
Monard, *Biochem. Pharmacol.* 36:1389–1392, 1987.
Thoenen et al., *Rev. Physiol. Biochem. Pharmacol*, 109:145–178, 1987.
Whittemore et al., *J. Neurosci.* 7:244–251, 1987.
Baskin et al., *Ann. Rev. Physiol.* 49:335–347, 1987.
Derynck, *Cell* 54:161:170, 1988.
Rosenberg et al., *Science* 242:1575–1578, 1988.
Walicke, *J. Neurosci*, 8:2618–2627, 1988.
Mouton et al., *Brain Research* 444:104–108, 1988.
Stockli et al., *Nature* 342:920–923, 1989.
Yamamori et al., *Science* 246:1412–1416, 1989.
Oltersdorf et al., *Nature* 341:144–147, 1989.
Whitson, et al., *Science* 243:1488–1490, 1989.
Hama et al., *Neurosci. Lett.* 104:340–344, 1989.
Hefti et al., *Neurobiol. Aging* 10:515–533, 1989.
Lin et al., *Science* 246:1023–1025, 1989.
Honjo et al., *Steroid Biochemistry* 34:521–524, 1989.
Gall et al., *Science* 245:758–761, 1989.
Kovesdi et al., *Biochem. Biophys. Res. Commun.* 172:850–854, 1990.
Kamegai, *Neuron* 2:429–436, 1990.
Hohn et al., *Nature* 344:339–341, 1990.
Fallon et al., *Growth Factors* 2:241–250, 1990.
Spranger et al., *Eur. J. Neurosci.* 2:69–76, 1990.
Maisonpierre et al., *Neuron* 5:501–509, 1990.
Ernfors et al., *Neuron* 5:511–526, 1990.
Rosenthal et al., *Neuron* 4:767–773, 1990.
Hallbrook et al., *Neuron* 6:845–858, 1991.
Berkemeier et al., *Neuron* 7:857–866, 1991.
Woolley et al., *Journal of Neuroscience* 12:2549–2554, 1992.
Gibbs et al., *Society for Neuroscience Abstracts* 19:5, 1993.
Wright et al., *Int. J. Dev. Neuroscience* 5:305–311, 1987.

(List continued on next page.)

Primary Examiner—Frederick Krass
Assistant Examiner—Donna Jague
(74) Attorney, Agent, or Firm—Bromberg & Sunstein LLP

(57) ABSTRACT

The present invention provides methods of conferring protection on a population of cells associated with ischemia in a subject following an ischemic event, comprising: (a) providing an estrogen compound; and (b) administering the effective amount of the compound over a course that includes at least one dose within a time that is effectively proximate to the ischemic event, so as to confer protection on the population of cells. Novel methods are provided for the intravenous administration of an estrogen compound. Examples of ischemic events treatable according to the invention are cerebrovascular disease or stroke, subarachnoid subhemorrhage, myocardial infarct, surgery and trauma. A method of treating ischemic damage utilizing non-sex hormones is also provided.

23 Claims, 9 Drawing Sheets

OTHER PUBLICATIONS

Jones, *Metabolic* Brain Disease 3:1–18, 1988.
Mizoguchi et al., *Neuroscience Letters* 138:157–160, 1992.
Honjo et al., *J. Steroid Biochem. Molec. Biol* 41:633–635, 1992.
Emerson et al., *Brain Research* 608:95–100, 1993.
Wroblewski et al., *Proc. Soc. Exp. Biol. Med* 90:210–213, 1955.
Black et al., *Exp. Cell Research* 35:9–13, 1964.
Oldendorf, *Brain Res.* 24:37–46, 1970.
Oldendorf, *Am. J. Physiol.* 221:1629–1638, 1971.
Fonnum, *J. Neurochem.* 24:407–409, 1975.
Kolbe et al., *Biochemistry & Biophysics* 73:378–382, 1976.
Keller et al., *Archives of Pharmacology* 294:213–215, 1976.
Perez–Polo et al., *Life Sci.* 21:1535–1543, 1977.
Luine et al., *Brain Research* 191:273–277, 1980.
Barde et al., *EMBO J.* 1:549–553, 1982.
Fallon et al., *Science* 224:1107–1109, 1984.
Morrison et al., *Prc. Nat'l. Acad. Sci. U.S.A.* 83:7537–7541, 1986.
Morse et al., *Experimental Neurology* 94:649–658, 1986.
Aizeman et al., *Proc. Nat'l Acad. Sci. U.S.A.* 83:2263–2266, 1986.
Fillet et al., *Psychoneuroendocrinology* 11:337–345, 1986.
Morrison et al., *Science* 238:72–75, 1987.
Monard, *Biochem Pharmacol.* 36:1389–1392, 1987.
Thoenen et al., *Rev. Physiol. Biochem. Pharmacol.* 109:145–178, 1987.
Whittemore et al., *J. Neurosci.* 7:244–251, 1987.
Baskin et al., *Ann. Rev. Physiol.* 49:335–347, 1987.
Derynck, *Cell* 54:161–170, 1988.
Rosenberg et al., *Science* 242:1575–1578, 1988.
Walicke, *J. Neurosci.* 8:2618–2627, 1988.
Mouton et al., *Brain Research* 444:104–108, 1988.
Stockli et al., *Nature* 342:920–923, 1989.
Yamamori et al., *Science* 246:1412–1416, 1989.
Oltersdorf et al., *Nature* 341:144–147, 1989.
Whitson et al., *Science* 243:1488–1490, 1989.
Hama et al., *Neursci. Lett.* 104:340–344, 1989.
Hefti et al., *Neurobiol. Aging* 10:515–533, 1989.
Lin et al., *Science* 246:1023–1025, 1989.
Honjo et al., *Steroid Biochemistry* 34:521–524, 1989.
Gall et al., *Science* 245:758–761, 1989.
Kovesdi et al., *Biochem. Biophys. Res. Commun.* 172:850–854, 1990.
Kamegai, *Neuron* 2:429–436, 1990.
Hohn et al., *Nature* 344:339–341, 1990.
Fallon et al, *Growth Factors* 2:241–250, 1990.
Spranger et al., *Eur. J. Neurosci.* 2:69–76, 1990.
Maisonpierre et al., *Neuron* 5:501–509, 1990.
Ernfors et al., *Neuron* 5:511–526, 1990.
Rosenthal et al., *Neuron* 4:767–773, 1990.
Hallbrook et al., *Neuron* 6:845–858, 1991.
Berkemeier et al., *Neuron* 7:857–866, 1991.
Woolley et al., *Journal of Neuroscience* 12:2549–2554, 1992.
Gibbs et al., *Society for Neuroscience Abstracts* 19:5, 1993.
Wright et al., *Int. J. Dev. Neuroscience* 5:305–311, 1987.
Jones, *Metabolic Brain Disease* 3:1–18, 1988.
Mizoguchi et al., *Neuroscience Letters* 138:157–160, 1992.
Honjo et al., *J. Steroid Biochem. Molec. Biol.* 41:633–635, 1992.
Emerson et al., *Brain Research* 608:95–100, 1993.
Draper, Michael W., et al, "A Controlled Trial of Raloxifene (LY139481) HCl:Impact on Bone Turnover and Serum Lipid Profile in Healthy Postmenopausal Women", *Journal of bone and Mineral Research*; vol. 11, 1996.
Evans, Glenda, et al, "The Effects of Raloxifene on Tibia Histomorphometry in Ovariectomized Rats", *Endocrinology*, 1345–2283, 1994.
Sato, Masahiko, et al, "Dual–Energy X–ray Absorptiometry of Raloxifene Effects ont he Lumbar Vertebrae and Femora of Ovariectomized Rats", *Journal of Bone and Mineral Research*, vol. 9, No. 5, 1994.
Sato, Masahiko, et al, "Longitudinal and Cross–Section Analysis of Raloxifene Effect on Tibiae from Ovariectomized Aged Rats",*The Journal of Pharmacology and Experimental Therapeutics*, 272:1252–1259, 1995.
Wroblewski et al., *Proc. Soc. Exp. Biol. Med.* 90:210–213, 1955.
Black et al., *Exp. Cell Research* 35:9–13, 1964.
Oldendorf, *Brain Res.* 24:37–46, 1970.
Oldendorf, *Am. J. Physiol.* 221:1629–1638, 1971.
Fonnum, *J. Neurochem.* 24:407–409, 1975.
Kolbe et al., *Biochemistry & Biophysics* 73:378–382, 1976.
Keller et al., *Archives of Pharmacology* 294:213–215, 1976.
Perez–Polo et al., *Life Sci.* 21:1535–1543, 1977.
Luine et al., *Brain Research* 191:273–277, 1980.
Barde et al., *EMBO J.* 1L549–553, 1982.
Fallon et al., *Science* l224:1107–1109, 1984.
Morrison et al., *Prc. Nat'l. Acad. Sci. U.S.A.* 83:7537–7541, 1986.
Morse et al., *Experimental Neurology* 94:649–658, 1986.
Aizeman et al., *Proc. Nat'l. Acad. Sci. U.S.A.* 83:2263–2266, 1986.
Fillet et al., *Psychoneuroendocrinology* 11:337–345, 1986.
Morrison et al., *Science* 238:72–75, 1987.
Monard, *Biochem. Pharmacol.* 36:1389–1392, 1987.
Thoenen et al., *Rev. Physiol. Biochem. Pharmacol.* 109:145–178, 1987.
Whittemore et al., *J. Neurosci.* 7:244–251, 1987.
Baskin et al., *Ann. Rev. Physiol.* 49:335–347, 1987.
Derynck *Cell* 54:161–170, 1988.
Rosenberg et al., *Science* 242:1575–1578, 1988.
Walicke, *J. Neurosci.* 8:2618–2627, 1988.
Mouton et al., *Brain Research* 444:104–108, 1988.
Stockli et al., *Nature* 342:920–923, 1989.
Yamamori et al., *Science* 246:1412–1416, 1989.
Oltersdorf et al., *Nature* 341:144–147, 1989.
Whitson et al., *Science* 243:1488–1490, 1989.
Hama et al., *Neurosci. Lett.* 104:340–344, 1989.
Hefti et al., *Neurobiol. Aging* 10:515–533, 1989.
Lin et al., *Science* 246:1023–1025, 1989.
Honjo et al., *Steroid Biochemistry* 34:521–524, 1989.
Gall et al., *Science* 245:758–761, 1989.
Kovesdi et al., *Biochem. Biophys. Res. Commun.* 172:850–854, 1990.
Kamegai, *Neuron* 2:429–436, 1990.
Hohn et al., *Nature* 344:339–341, 1990.
Fallon et al., *Growth Factors* 2:241–250, 1990.
Spranger et al., *Eur. J. Neurosci* 2:69–76, 1990.
Maisonpierre et al., *Neuron* 5:501–509, 1990.
Rosenthal et al., *Neuron* 4:767–773, 1990.
Hallbrook et al., *Neuron* 6:845–858, 1991.
Berkemeier et al., *Neuron* 7:857–866, 1991.
Woolley et al., *Journal of Neuroscience* 12:2549–2554, 1992.

Gibbs et al., *Society for Neuroscience Abstracts* 19:5. 1993.
Wright et al., *Int. J. Dev. Neuroscience* 5:305–311, 1987.
Jones, *Metabolic Brain Disease* 3:1–18, 1988.
Mizoguchi et al., *Neuroscience Letters* 138:157–160, 1992.
Honjo et al., *J. Steroid Biochem. Molec. Biol.* 41:633–635, 1992.
Emerson et al., *Brain Research* 608:95–100. 1993.
Siesjo, Bo K., M.D.,*Pathophysiology and treatment of focal cerebral ischemia, Neurosurgery*, vol. 7, 1992.
Falkeborn, Margareta et al., *Hormone Replacement Therapy and the Risk of Stroke*, Arch Interna Med, vol. 153, 1993.
Schehr, Robert S., *New treatments for acute stroke*, Nature Biotechnology, vol. 14, 1996.
Stampler, Meir J. et al., Postmenopausal Estrogen Therapy and Cardiovascular Disease, *The New England Journal of Medicine*, 1991.
Wren, Barry G., The effect of oestrogen on the female cardiovascular, *The Medical Journal of Australia*, vol. 157, 1992.
Patent Abstract of Japan; Applicant: Oyo Seikagaky Kenkyusho; Inventor: Yagi Kunio; Publication No.: 0517883, Jul. 20, 1993.
Patent Abstract of Japan; Applicant: Yagi Kunio; Inventor: Yagi Junio; Publication No. 08165242, Jun. 25, 1996.
Komburo, Ericka, et al "Inhibition of Peroxidations of Lipids and Membranes by Estrogens" *Journal of Physical Organic Chemistry*, vol. 3, 309–315 (1990).
Lacort, Mercedes, et al., "Protective Effect of Estrogens and Catechloestrogens Against Peroxidative Membrane Damage in vitro", *Lipids*, vol. 30, No. 2 (1995).
Renaud, S., "Thrombosis and Atherosclerosis Prevention by Estrogens in Hyperlipemic Rats" *Athrosclerosis*, vol. 12, 467–473 (1970).
Claus, S., et al., Influence of Hormone Application by Subcutaneous Injections or Steroid–Containing Silastic Implants on Human Benign Hyperplastic Prostate Tissue Transplanted into male Nude Mice, The Prostate, 22:199–215, 1993.
P.E. Cohen, et al. Silastic implants for delivery of oestradiol to mice, Journal of Reproduction and Fertility, 99:219–223, 1993.
Medlock, K.L., et al. Progesterone and Estradiol Interaction in the Regulation of Rate Uterine Weight and Estrogen Receptor Concentration, Proc. Sox. Exp. Biol. Med., 205(2), pp. 146–153, Feb., 1994.
Petersen, S.L., et al. Effects of Estrogen and Progesterone on Luteinizing Hormone–releasing Hormone Messenger Ribonucleic Acid Levels: Consideration of Temporal and Neuronatomical Variables, Endocrinology, 136(8), pp 3604–3610, Aug., 1995.
Skinner, D.C.,et al., The Progesterone Blockade of the Luteinizing Hormone Surge Is Overcome by RU486, J. Neuroendocrinol. 11(8): 637–641, Aug., 1999.
Kim et al., Beta Estradiol Prevents Dysfunction of Canine Coronary Endothelium and Myocardium and Reperfusion Arrhythmias After Brief Ischemia/Reperfusion, Circulation vol. 94, No. 11, pp. 2901–2908, Dec. 1996.*
Renaud, S., "Thrombosis and Atherosclerosis Prevention by Estrogens in Hyperlipemic Rats", Atherosclerosis, vol. 12, pp. 467–473 (1970).
Clark, James H., et al., "The Agonistic and Antagonistic effects of Short Acting Estrogens: A Review", Pharmacy Ther., vol. 21, pp. 429–453 (1983).

Namba, H., et al., "Acute administration of high doses of estrogen increases glucose utilization throughout brain", Brain Research, vol. 291, pp. 391–394 (1984).
Niki, Etsuo, "Antioxidants in Relation to Lipid Peroxidation", Chemistry and Physics of Lipids, vol. 44, p. 227 (1987).
Sugioka, Katsuaki, et al., "Estrogens as natural antioxidants of membrane phospholipid peroxidation", Federation of European Biochemical Societies, vol. 210, No. 1, pp. 37–39 (1987).
Paganini–Hill, Annlia, et al., "Postmenopausal osestrogen treatement and stroke: a prospective study", Brit. Med. Journal., vol. 297, 519–522, (1988).
Sherwin, Barbara B. "Estrogen and/or Androgen Replacement Therapy and Cognitive Functioning in Surgically Menopausal Women," Psychoneuroendocrinology, vol. 13, pp. 345–357 (1988).
Honjo, Hideo, et al., "In Vivo Effects by Estrone Sulfate on the Central Nervous System–Senile Dementia (Alzheimer's Type)" Steroid Biochemistry, vol. 34, pp. 521–524 (1989).
Dimlich, R.V.W., et al, "Effects of a 21–Aminosteroid (U–74006F) on Cerebral Metabolites and Edema After Severe Experimental Head Trauma", Advances in Neurology, vol. 52, pp. 365–375 (1990).
Jacobsen, E. Jon, et al, "Novel 21–Aminosteroids that Inhibit Iron–Dependent Lipid Peroxidation and Protect Against Central Nervous System Trauma", Journal Medical Chemistry, vol. 33, pp. 1145–1151 (1990).
Powell, Elizabeth M., et al., "Controlled Release of Nerver Growth Factor from a Polymeric Implant," Brain Research, vol. 515, pp. 309–311 (1990).
Sherwin, Barbara B. et al., "Estrogen and Cognitive Functioning in Surgically Menopausal Women," Annal of the New York Academy of Science, vol. 592, pp. 474–475 (1990).
Sherwin, Barbara B., et al., "Up–Regulatory Effect of Estrogen on Platelet 3H–Imipramine Binding Sites in Surgically Menopausal Women," Biol. Psychiatry, vol. 28, pp. 339–348 (1990).
Simpkins, James W., et al., "A Brain–Enhanced Chemical Delivery System for Gonadal Steroids: Implications for Neurodegenerative Diseases," in Novel Procedures for the Treatment of Alzheimer's Disease, Meyer et al. Eds., pp. 197–212, Plenum Press (1990).
Hall, Edward D., et al., "Sex Differences in Postischemic Neuronal Necrosis in Gerbils" Journal of Cerebral Blood Flow and Metabolism, vol. 11, pp. 292 (1991).
Sherwin, Barbara B., "The Impact of Different Doses of Estrogen & Progestin on Mood and Sexual Behavior in Postmenopausal Women," Journal of Clinical Endocrinology and Metabolism, vol. 72, pp. 336–343 (1991).
Stampler, Meir J., et al., "Postmenopausal Estrogen Therapy and Cardiovascular Disease", The New England Journal of Medicine (1991).
Hall, Edward D., PhdD., "The neuroprotective pharmacology of methylprednisolene", Journal of Neurosurgery, vol. 76, pp. 13–22 (1992).
Kostanyan, Amalia, et al., "Rat brain glycolysis regulation by estradiol–17β" Biochimica et Biophysica Acta, vol. 1133, pp. 301–306 (1992).

Schehr, Robert S., "New treatments for acute stroke", Nature Biotechnology, vol. 14, pp. 1549–1554 (1996).

Simpkins, James W., et al., "Estrogens may reduce mortaility and ischemic damage caused by middle cerebral artery occlusion in the female rat", Journal of Neurosurgery, vol. 87, pp. 724–730; (Nov. 1997).

Wang, Giong, et al., "Estrogen Provides Neuroprotection in Transient Forebrain Ischmia Through Perfusion–Independent Mechanisms in Rats", Stroke, vol. 30, pp. 630–637 (1999).

* cited by examiner

METHODS OF PREVENTION AND TREATMENT OF ISCHEMIC DAMAGE

TECHNICAL FIELD

The present invention relates to the protection of cells that would otherwise die as a result of an ischemic event.

BACKGROUND ART

Ischemia is an acute condition associated with an inadequate flow of oxygenated blood to a part of the body, caused by the constriction or blockage of the blood vessels supplying it. Ischemia occurs any time that blood flow to a tissue is reduced below a critical level. This reduction in blood flow can result from: (i) the blockage of a vessel by an embolus (blood clot); (ii) the blockage of a vessel due to atherosclerosis; (iii) the breakage of a blood vessel (a bleeding stroke); (iv) the blockage of a blood vessel due to vasoconstriction such as occurs during vasospasms and possibly, during transient ischemic attacks (TIA) and following subarachnoid hemorrhage. Conditions in which ischemia occurs, further include (i) myocardial infarction; (ii) trauma; and (iii) during cardiac, thoracic and neurosurgery (blood flow needs to be reduced or stopped to achieve the aims of surgery). During myocardial infarct, stoppage of the heart or damage occurs which reduces the flow of blood to organs, and ischemia results. Cardiac tissue itself is also subjected to ischemic damage. During various surgeries, reduction of blood flow, clots or air bubbles generated can lead to significant ischemic damage.

When an ischemic event occurs, there is a gradation of injury that arises from the ischemic site. The cells at the site of blood flow restriction, undergo necrosis and form the core of a lesion. A penumbra is formed around the core where the injury is not immediately fatal but progresses slowly toward cell death. This progression to cell death may be reversed upon reestablishment of blood flow within a short time of the ischemic event.

Focal ischemia encompasses cerebrovascular disease (stroke), subarachnoid hemorrhage (SAH) and trauma. Stroke is the third leading cause of morbidity in the United States, with over 500,000 cases per year, including 150,000 deaths annually. Post-stroke sequelae are mortality and debilitating chronic neurological complications which result from neuronal damage for which prevention or treatment are not currently available.

Following a stroke, the core area shows signs of cell death, but cells in the penumbra remain alive for a period of time although malfunctioning and will, in several days, resemble the necrotic core. The neurons in the penumbra seem to malfunction in a graded manner with respect to regional blood flow. As the blood flow is depleted, neurons fall electrically silent, their ionic gradients decay, the cells depolarize and then they die. Endothelial cells of the brain capillaries undergo swelling and the luminal diameter of the capillaries decrease. Associated with these events, the blood brain barrier appears to be disrupted, and an inflammatory response follows which further interrupts blood flow and the access of cells to oxygen.

The effects of a stroke on neurons result from the depletion of energy sources associated with oxygen deprivation which in turn disrupts the critically important ion pumps responsible for electrical signaling and neurotransmitter release. The failure of the ATP-dependant ion specific pumps to maintain ion gradients through active transport of sodium, chlorine, hydrogen, and calcium ions out of the cell and potassium ions into the cell results in a series of adverse biochemical events. For example, increase in intracellular calcium ion levels results in: (I) the production of free radicals that extensively damage lipids and proteins; (ii) the disruption of calcium sensitive receptors such as the N-methyl D-aspartate (NMDA) and the α-amino-3-hydroxy-5-methyl-4-isoxazoleproprionic acid (AMPA) synaptic glutamate receptors; (iii) the swelling of cells with water as a result of abnormal accumulation of ions; and (iv) the decrease in intracellular pH. The alteration in metabolism within the cell further results in the accumulation of ions in the cells as energy sources are depleted. For example, anaerobic glycolysis that forms lactic acid, replaces the normal aerobic glycolysis pathways in the mitochondria. This results in acidosis that results in further accumulation of calcium ions in the cell.

Despite the frequency of occurrence of ischemia (including stroke) and despite the serious nature of the outcome for the patient, treatments for these conditions have proven to be elusive. There are two basic approaches that have been undertaken to rescue degenerating cells in the penumbra. The first and most effective approach to date has been the identification of blood clot dissolvers that bring about rapid removal of the vascular blockage that restricts blood flow to the cells. Recombinant tissue plasminogen activator (TPA) has been approved by the Federal Drug Administration for use in dissolving clots that cause ischemia in thrombotic stroke. Nevertheless, adverse side effects are associated with the use of TPA. For example, a consequence of the breakdown of blood clots by TPA treatment is cerebral hemorrhaging that results from blood vessel damage caused by the ischemia. A second basic approach to treating degenerating cells deprived of oxygen is to protect the cells from damage that accumulates from the associated energy deficit. To this end, glutamate antagonists and calcium channel antagonists have been most thoroughly investigated. None of these have proven to be substantially efficacious but they are still in early clinical development. The pathophysiology and treatment of focal cerebral ischemia has been reviewed by B.K. Seisjo, J. Neurosurgery, 1992, vol. 77, p. 169–184 and 337–354.

In addition to the targets of drug development described by Seisjo (1992), epidemiological studies have shown that women undergoing hormone replacement therapy with estrogen and progesterone experienced a reduction in the incidence and severity of heart disease. This correlation was further investigated for stroke with mixed results. A 10-year epidemiological study on 48,000 women reported by Stampfer et al. (New England Journal of Medicine 1991, vol. 325, p. 756) concluded that there was a correlation between use of estrogen and decrease in incidence of coronary heart disease, but no decrease in the incidence of stroke was observed. In contrast, a report by Wren (The Medical Journal of Australia, 1992, vol. 157, p. 204) who reviewed 100 articles directed to the question as to whether estrogens reduce the risk of atherosclerosis and myocardial infarction, concluded that estrogens in hormone replacement therapies significantly reduce the incidence of myocardial infarction and stroke and may accomplish this at the site of the blood vessel wall. This conclusion was further supported by Falkeborn et al. Arch Intern. Med., 1993, vol. 153, 1201. The above correlation between estrogen replacement therapy and reduced incidence of stroke relies on epidemiological data only. No biochemical data were analyzed to interpret or support these conclusions, nor is there any information as to reduction in ischemic lesion or morbidity with hormone use. Furthermore, these studies were restricted to the patients receiving long-term hormone replacement treatment. No studies were performed on patients who might be administered estrogen therapeutically shortly before, during, or after a stroke. Furthermore, the studies were limited to estrogens utilized in estrogen replacement therapy. No studies were performed on any non-sex related estrogens that might be used in treating males or females.

Studies have been conducted on the neuroprotective effects of steroids in which glucocorticosteroid for example was found to have a positive effect in reducing spinal cord injury but had a negative effect on hippocampal neurodegeneration. For example, Hall (J. Neurosurg vol. 76, 13–22 (1992)) noted that the glucocorticoid steroid, methylprednisolone, believed to involve the inhibition of oxygen free radical-induced lipid peroxidation, could improve the 6-month recovery of patients with spinal cord injury when administered in an intensive 24-hour intravenous regimen beginning within 8 hours after injury. However, when the steroid was examined for selective protection of neuronal necrosis of hippocampal neurons, it was found that the hippocampal neuronal loss was significantly worsened by glucocorticoid steroid dosing suggesting that this hormone is unsuitable for treating acute cerebral ischemic. Hall reported that substitution of a complex amine on a non-glucocorticoid steroid in place of the 21-hydroxyl functionality results in an enhancement of lipid anti-oxidant activity. No data were provided concerning the behavior of this molecule in treating ischemic events or in neuroprotection of neurons in the brain. Additionally, free radical scavenging activity has been reported for a lazaroid, another non-glucocorticoid steroid having a substituted 21-hydroxyl functionality, but there is no evidence that this compound is significantly efficacious for treating stroke or other forms of ischemia.

There is a need for effective treatments for stroke and other forms of ischemia that are safe and may be administered preventatively to men and women who are susceptible to such conditions, and may further be used after the ischemia has occurred so as to protect cells from progressive degeneration that is initiated by the ischemic event. There is further a need for therapeutic strategies to treat victims of stroke or other forms of ischemic events such as myocardial infarction, in which the active drug enters the bloodstream very rapidly, reaching peak levels within minutes. As estrogen compounds are reasonably insoluble, there is further a need for effective methodologies to dissolve and deliver the compound, preferably within an intravenous vehicle.

SUMMARY OF THE INVENTION

The invention satisfies the above need. Novel methods are provided for prevention and treatment of ischemic damage using estrogen compounds.

A preferred embodiment of the invention provides a method for conferring protection on a population of cells associated with an ischemic focus, in a subject following an ischemic event that includes the steps of providing an estrogen compound as sodium sulfate 17β-estradiol in an intravenous formulation so as to confer protection on the population of cells. Further embodiments include selecting a proximate time for administering the effective dose of the estrogen compound that is prior to the ischemic event. Alternatively, the estrogen compound may be administered within an effective proximate time after the ischemic event. The method of the invention may be applied to any of a cerebrovascular disease, subarachnoid hemorrhage, myocardial infarct, surgery, and trauma. In particular, when the ischemic event is a stroke, the protected cells include at least one of neurons and endothelial cells.

The method utilizes an estrogen compound which may include alpha isomers or beta isomers of estrogen compounds. Examples of different isomers are provided wherein the estrogen compound is selected from the group consisting of 17α-estradiol and 17β-estradiol.

In a preferred embodiment of the invention, a method is provided for protecting cells in a subject from degeneration during or after an ischemic event. The steps of the method include identifying a susceptible subject, providing an effective dose of an estrogen compound prior to or after the ischemic event, and protecting cells from degeneration otherwise occurring in the absence of the estrogen compound.

In a further embodiment of the invention, a method is provided for treating stroke in a subject, including the steps of providing an effective dose of an estrogen compound in a pharmaceutical formulation and administering the formulation to the subject so as to reduce the adverse effects of the stroke.

In another embodiment, a method is provided for conferring protection on a population of cells associated with an ischemic focus, in a subject following an ischemic event, comprising: (a) selecting a sodium sulfate form of an estrogen compound; (b) formulating the sodium sulfate of the estrogen compound in an intravenous delivery vehicle; and (c) administering the formulation to a subject so as to reduce the adverse effects of the ischemic event. In certain aspects of this embodiment, (c) further comprises administering an effective amount of the compound over a course that includes at least one dose within a time that is effectively proximate to the ischemic event, so as to confer protection on the population of cells.

BRIEF DESCRIPTION OF THE DRAWINGS

These and other features, aspects, and advantages of the present invention will be better understood with reference to the following description, appended claims, and accompanying drawings, where:

DETAILED DESCRIPTION OF SPECIFIC EMBODIMENTS

Figure 1:
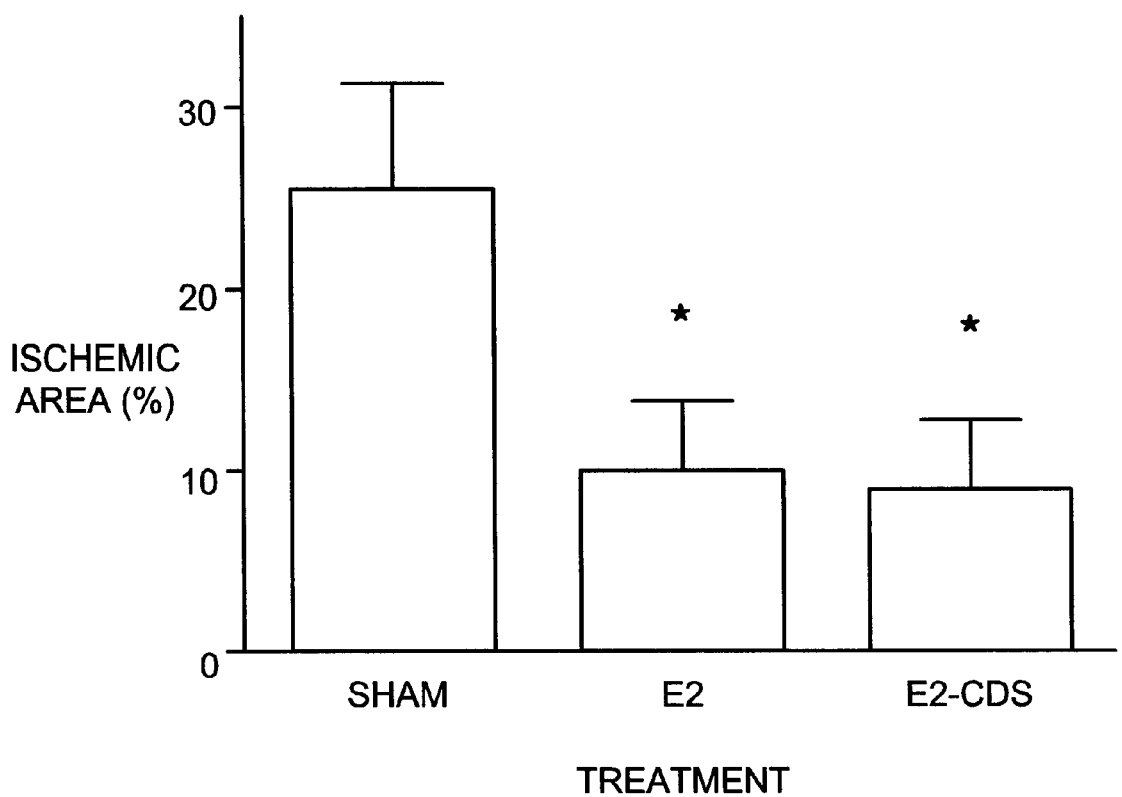
FIG. 1 shows the effects of pretreatment of ovariectomized rats, with 17β-estradiol, initiated 24 hours prior to ischemia induced by middle cerebral artery occlusion (MCAO); where the 17β-estradiol is administered as a subcutaneous 5 mm Silastic® implant (E2) or via the estradiol-chemical delivery system (E2-CDS) (1 mg/kg body weight) and a control is provided (a sham pellet). Values are given as the mean plus and minus the standard error of the mean (±SEM) for the percent ischemic area in 3 brain slices. The asterisk indicates that the observed p value was less than 0.05 (*=p<0.05) vs. sham group. The number of samples for sham=6, for 17β-estradiol=8, and for E2-CDS groups=10.

The invention provides an effective treatment for stroke and other forms of ischemia that may safely be administered to men and women so as to protect cells from progressive degeneration that is initiated by the ischemic event.

Estrogen compounds are defined here and in the claims as any of the structures described in the 11th edition of "Steroids" from Steraloid Inc., Wilton, N.H., incorporated herein by reference. Included in this definition are non-steroidal estrogens described in the aforementioned reference. Other estrogens included in this definition are estrogen derivatives, estrogen metabolites, estrogen precursors, and modifications of the foregoing as well as molecules capable of binding cell associated estrogen receptor as well as other molecules where the result of binding triggers a characteristic estrogen effect. Any diastereomer or enantiomer of compounds described herein is included in the definitions herein. Also included are mixtures of more then one estrogen. The term "estradiol" or "estrogen" is included in the definition of estrogen compound.

β-estrogen and α-estrogen are isomers of estrogen.

The term "E2" is synonymous with β-estradiol, 17β-estradiol, $E_2$, and β-$E_2$.

An "animal subject" is defined here and in the claims as a higher organism including humans.

The term "non-sex hormone" is defined here and in the claims an estrogen hormone having diminished, minimal or no sex-related effect on the subject.

Estrogen compounds are here shown to protect cells from degeneration in the penumbra of the ischemic lesion (Examples 1 and 2). Estrogen compounds are further shown to be protective of a plurality of cell types, including neuronal cells and endothelial cells (Examples 1–3). According to the invention, estrogen compounds may be used to protect cells from the effects of oxygen deprivation and glucose deprivation and consequently from energy deprivation associated with ischemia.

In an embodiment of the invention, a method of treatment is provided that is suitable for human male and female subjects and involves administering an effective dose of estrogen either before or after a stroke has occurred.

In certain circumstances according to the invention, it is desirable to administer estrogen prior to a predicted ischemic event. Such circumstances arise when, for example, a subject has already experienced a stroke. In this case, the subject will have an increased probability of experiencing a second stroke. Subjects who are susceptible to transient ischemic attacks also have an increased risk of a stroke. Subjects who suffer a subarachnoid hemorrhage may experience further ischemic events induced by vasospasms that constrict the blood vessels. Subjects who experience trauma to organs such as the brain are also susceptible to an ischemic event. The above situations exemplify circumstances when a subject would benefit from pretreatment with an estrogen compound. Such pretreatment may be beneficial in reducing the adverse effects of a future ischemic event when administered in the short term, such as within 24 hours before the event (Example 1) or in the long term, where administration begins immediately after an event such as a stroke and continues prophylactically for an extended period of time. An example of time of administration for prophylactic use may extend from days to months depending of the particular susceptibility profile of the individual. In these circumstances, a course of at least one dose of estrogen may be administered over time so that an effective dose is maintained in the subject. For short term treatments, parenteral administration may be used as an alternative to the delivery of a dose by any of the routes specified below. The optimal dose of estrogen compound for prophylactic use should provide a plasma concentration of 10–500 pg/ml of estrogen compound, however higher doses are also acceptable. In these circumstances, the use of non-sex estrogen compounds such as the α-estrogen isomers are of particular utility in men and women because the sex-related functions of the hormone are avoided.

According to embodiments of the invention, estrogen compounds are effective in reducing the adverse effects of an ischemic event such as cerebrovascular disease, subarachnoid hemorrhage, or trauma. Accordingly, the compound is administered as soon as possible after initiation of the event and preferably within 12 hours, more particularly, within 5 hours following the event. It is desirable that an increased concentration of estrogen compound be maintained in the plasma for at least several hours to several days following the ischemic event. The increased concentration of estrogen compound in the plasma should be in the range of 10–12,000 pg/ml of estrogen compound.

The present invention demonstrates for the first time that pretreatment with estrogens or early post-treatment of an estrogen compound can significantly reduce the size of the necrotic area following an ischemic event. This effect of pretreatment with an estrogen compound is independent of the isomeric form and the route of administration of the estrogen compound. α-isomers of estrogen have been shown to be as effective as β-isomers of estrogen in protecting cells from the effects of ischemia. The method as exemplified in Example 1 and FIGS. 1, 2 and 3 confirm that the protective activity of estrogen compounds is not dependent on the sex-related activity of the hormone (estrogenicity). α-isomers of estrogen compounds are non-sex hormones, yet these compounds are as effective at protecting the brain against ischemic damage as the β-isomers. Example 1 further demonstrates that the observed reduction in mortality of ovariectomized rats when treated with 17β-estradiol is not dependent on the route of administration, since the protective effect was similar when the same estrogen compound was administered as a subcutaneous implant or as an intravenous injection. Regardless of the route of administration or the formulation, the estrogen compounds have a remarkable effect on the ability of animals to survive an ischemic event.

The demonstration that estrogen is efficacious in protection of cells in an ischemic area is demonstrated in the examples below using rat models in which the middle cerebral artery (MCA) is experimentally occluded, middle cerebral artery occlusion (MCAO) model. This animal model is well known in the art to simulate an in vivo ischemic event such as may occur in a human subject. The experimental occlusion of the MCA causes a large unilateral ischemic area that typically involves the basal ganglion and frontal, parietal, and temporal cortical areas (Menzies et al. Neurosurgery 31, 100–106 (1992)). The ischemic lesion begins with a smaller core at the site perfused by the MCA and grows with time. This penumbral area around the core infarct is believed to result from a propagation of the lesion from the core outward to tissue that remains perfused by collateral circulation during the occlusion. The effect of a therapeutic agent on the penumbra surrounding the core of the ischemic event may be examined when brain slices are obtained from the animal. The MCA supplies blood to the cortical surfaces of frontal, parietal, and temporal lobes as well as basal ganglia and internal capsule. Slices of the brain are taken around the region where the greatest ischemic effect occurs. These regions have been identified as region B, C, and D in Examples 2 and 3. These regions are not as readily compensated by alternative sources of blood flow as are regions A and E. This is because the MCA is the terminal artery on which the lace of collateral arteries supplying the MCA-distributed area relies, thereby making the MCAO induced ischemia refractory to compensation. On the other hand, anastomoses between MCA and the anterior carotid artery (ACA) in region A and between MCA and the posterior carotid artery (PCA) in region E (Examples 1 and 2), may compensate for the MCA occlusion-induced ischemia as observed in the present study.

In order to study the effect of estrogen on the propagation of the lesion following an ischemic event, rats were ovariectomized and two weeks later were exposed to various estrogen preparations prior to or following MCAO (Examples 1 and 2). Untreated, ovariectomized rats had a mortality of 65%. Pretreatment with E2-CDS or 17β-estradiol (E2) itself decreased mortality to 16% and 22%, respectively. This marked reduction in mortality was accompanied by a reduction in the ischemic area of the brain from 25.6±5.7% in the untreated, ovariectomized rats to 9.1±4.2% and 9.8±4.0 in the E2-CDS or 17β-estradiol treated rat, respectively. Similarly, pretreatment with non-sex hormones, exemplified by 17α-estradiol, reduced ischemic area by 55 to 81% (Example 1). When administered 40 or 90 minutes after MCA occlusion, E2-CDS reduced ischemic area by 45–90% or 31%, respectively (Example 2). Non-sex hormones were also highly protective when administered following induction of ischemia. These results demonstrate the neuroprotective effect of estrogen compounds in the brain following an ischemic event.

Figure 6:
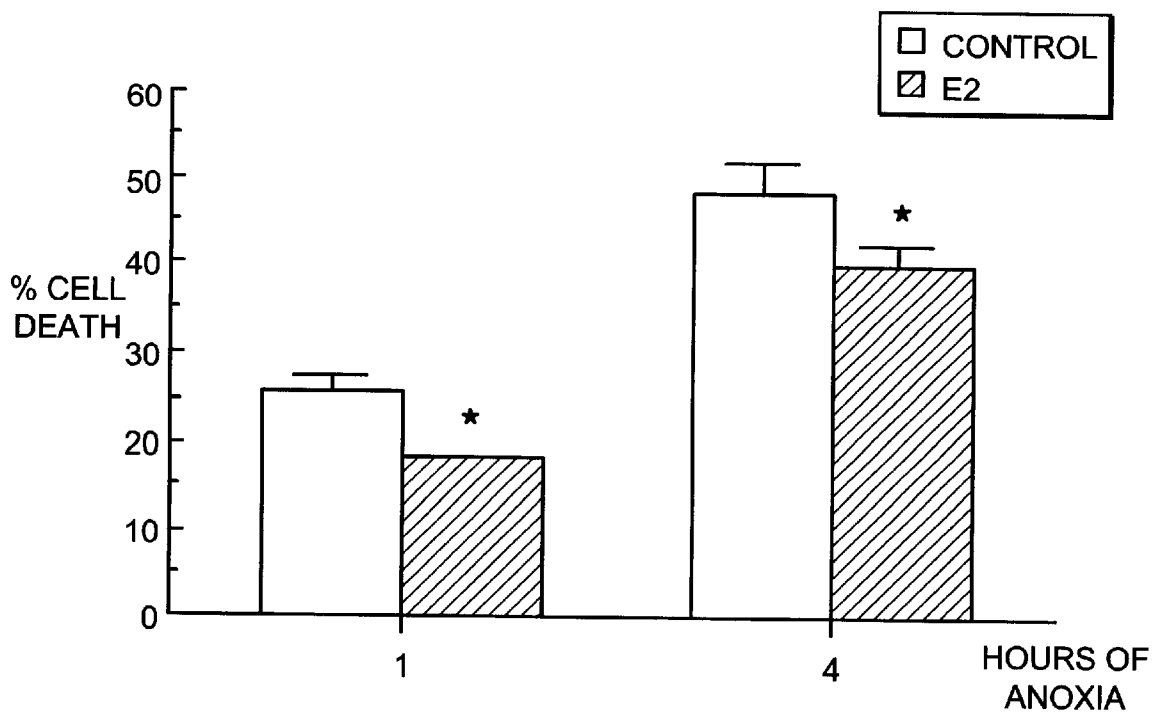
FIG. 6 is a bar graph that shows the effects of 17β-estradiol (2 nm) on BCEC mortality following anoxia. The control consists of the ethanol vehicle without estrogen. Cell media contained 200 mg % glucose. Culture dishes containing BCEC were placed in nitrogen filled chamber for 4 hours. Trypan blue staining was used to distinguish live cells from dead cells. Two cell countings at two different hemacytometer squares were averaged. Mean±SEM are depicted (n=8–12). *$p<0.05$ vs. corresponding vehicle control.
Figure 7:
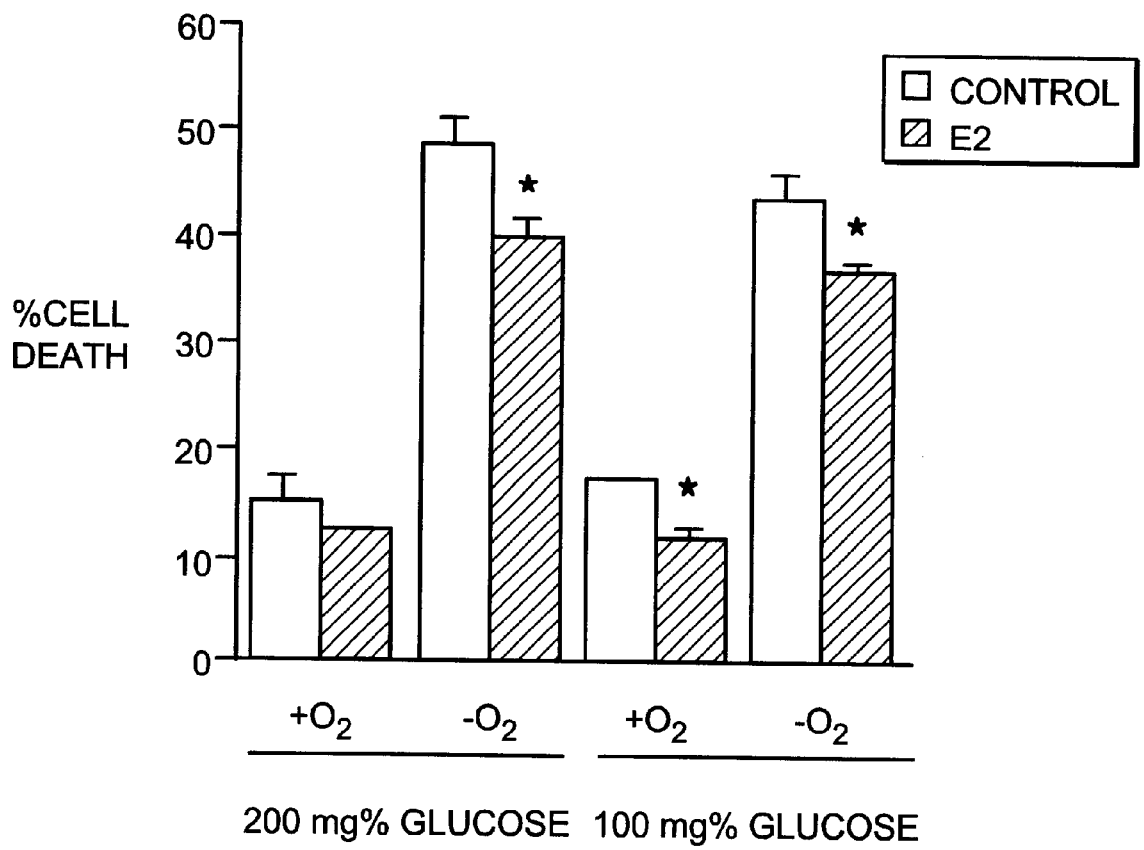
FIG. 7 is a bar graph that shows the effects of 17β-estradiol (2 nm) on BCEC mortality compared with a control (ethanol vehicle) following a combination treatment of both anoxia and hypoglycemia. Cell media contained 200 mg % or 100 mg % glucose. Culture dishes containing BCEC were placed in either an incubator or a nitrogen filled chamber for two hours. Trypan blue staining was used to distinguish live cells from dead cells. Two cell countings at two different hemacytometer squares were averaged. Mean±SEM are depicted (n=8.12). *<0.05 vs. corresponding vehicle control.

Reduction in available oxygen and glucose for energy metabolism is a feature of an ischemic event. This has a negative impact on the blood vessels that may be required to supply nutrients once the occlusion is reversed. The negative effect on blood vessels following ischemia further increases the long-term damage associated with the event. This effect can be reproduced in vitro as described in Example 3. In these circumstances, it has been shown here, estrogen compounds are capable of protecting brain capillary endothelial cells from cell death that would otherwise occur during hypoglycemia and anoxia during an ischemic event (FIGS. 5–7). As a consequence of this protection, the integrity of the vascular supply and the blood brain barrier is preserved by estrogen compounds such that following reperfusion of the brain after the ischemic event, blood flow and transport functions can once again occur.

Figure 9:
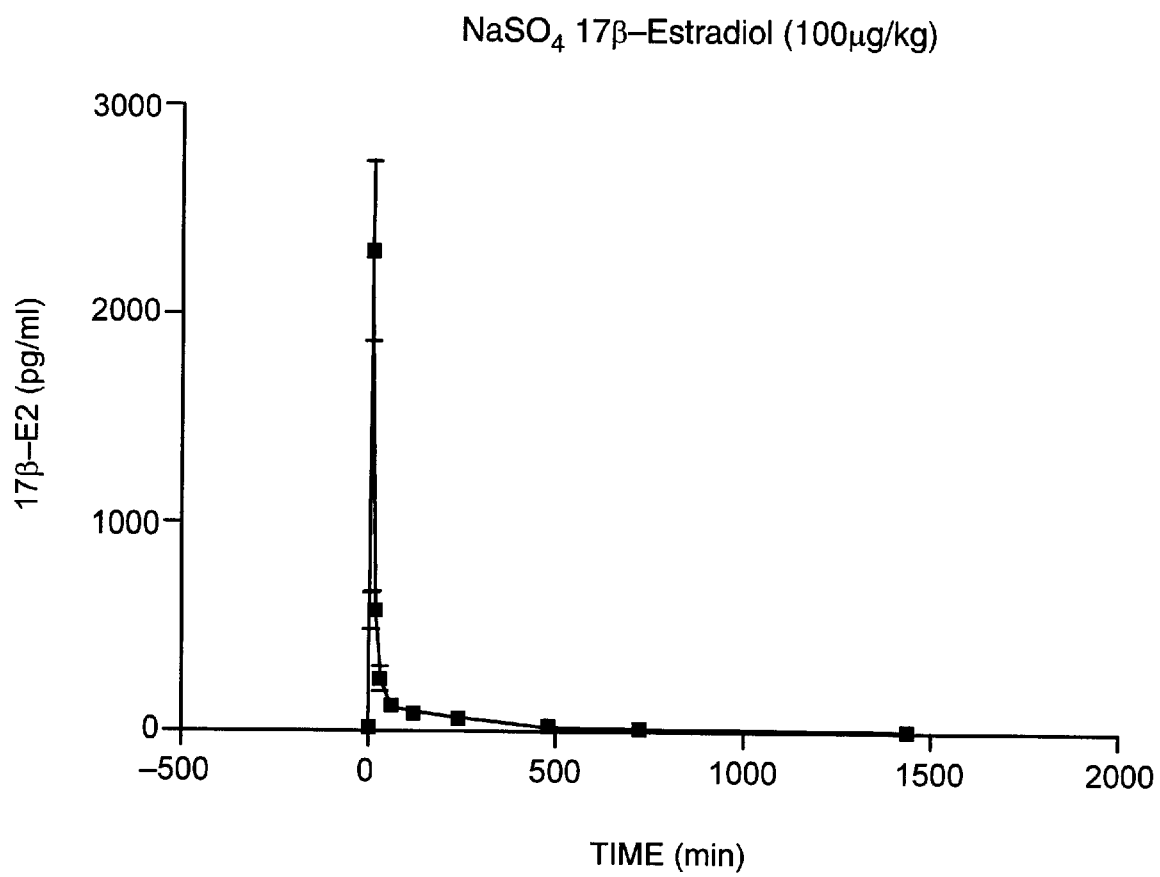
FIG. 9 is a graph that shows the effects of intravenous administration of sodium sulfate 17β-estradiol (at a dose of 100 µg/kg using a 100 µg/ml stock solution) on plasma concentrations of 17β-estradiol shown on the ordinate, as a function of time shown on the abscissa.

Estrogen compounds are shown here to be effectively delivered intravenously when dissolved as sodium sulfated compound (FIG. 9). This mode of delivery produced blood levels of approximately 2,500 pg/ml of the estrogen compound within 5 minutes.

EXAMPLES

Example 1

Measurement of the Effect of Estrogen Compounds Administered Prior to Ischemic Events.

Rats were used as experimental models to test the effects of estrogen in protecting against ischemic damage. To remove the naturally occurring source of estrogen, ovariectomies were performed prior to induction of ischemia.

Subsequent to the ovariectomy, rats were treated with an estrogen compound either by subcutaneous delivery with Silastic® tubes 24 hours prior to the MCA occlusion or by intravenous delivery as follows:

Subcutaneous sustained delivery: 17β- or 17α-estradiol was packed into 5 mm long Silastic® tubes (Dow-Corning, Midland, Mich.) according to the method of Mohammed et al. Ann. Neurol 18, 705–711, 1985. Sham (empty) tubes were similarly prepared as estrogen negative controls. The pellets were implanted subcutaneously (sc) into ovariectomized rats 24 hours prior to MCAO. 5 mm of Silastic® tubing containing estrogen resulted in plasma levels of about 100–200 pg/ml.

Intravenous (iv) delivery: 17β-estradiol was prepared for iv delivery using an estrogen-chemical delivery system (E2-CDS) as described in Brewster et al., Reviews in the Neurosciences 2, 241–285 (1990) and Estes et al., Life Sciences 40: 1327—1334 (1987). E2-CDS was complexed with hydroxypropyl-β-cyclodextrin (HPCD) (Brewster et al. J. Parenteral Science and Technology 43: 231–240, (1989)). The complexation achieved was 32 mg of E2-CDS per gram HPCD. In the first study, a single iv injection of E2-CDS (1 mg/kg body weight) was administered at 24 hours prior to MCAO. The control was administered HPCD only. The chemical delivery system is formulated so that the estrogen is slowly released from the carrier. This delivery system has been shown to effectively deliver estrogen in a sustained manner to the brain. Indeed, the dose of E2-CDS used in Examples 1 and 2 (1 mg/kg) is sufficient to provide 1000 pg/gm brain tissue at 24 hours post administration.

At 7 to 8 days after ovariectomy, a method for occluding the middle carotid artery was applied to the rat using modifications of the methods of Longa et al. (1989) Stroke, vol. 20, 84–91; and Nagasawa et al. (1989) Stroke, vol. 20, 1037–1043, with certain modifications, as described herein.

Animals were anesthetized with ketamine (60 mg/kg) and xylazine (10 mg/kg, intraperitoneal (ip)). Rectal temperature was monitored and maintained between 36.5 and 37.0° C. with a heat lamp throughout the entire procedure. The left carotid artery was exposed through a midline cervical incision. The left sternohyloid, sternomastoid, digastric (posterior belly) and the omohyloid muscles were divided and retracted. Part of the greater horn of the hyloid bone was cut to facilitate exposure of the distal external carotid artery (ECA). The common carotid artery (CCA), ECA, and internal carotid artery (ICA) were dissected away from adjacent nerves. The distal ECA and its branches, the CCA, and the pterygopalatine arteries were coagulated completely. A microvascular clip was placed on the ICA near skull base. A 2.5 cm length of 3-0 monofilament nylon suture was heated to create a globule for easy movement and blocking of the lumen of the vessel. This was introduced into the ECA lumen through the puncture. The suture was gently advanced to the distal ICA until it reached the clipped position. The microvascular clip was then removed and the suture was inserted until resistance was felt. The distance between the CCA bifurcation and the resistive point was about 1.8 cm. This operative procedure was completed within 10 minutes without bleeding. After the prescribed occlusion time (40 minutes), the suture was withdrawn from the ICA and the distal ICA was immediately cauterized. Animals that survived until the scheduled sacrifice time were sacrificed by decapitation. Scheduled post-ischemic sacrifices occurred at 6 hours, 24 hours and 1 week post MCAO (Table 1). For the 6-hour sample, animals were monitored continuously. For the 24-hour sample, animals were observed for about 4 hours and were then returned to their cage. Similarly, animals scheduled for the 1 week post-ischemic sacrifice were monitored for the first 4 hours after surgery and then daily thereafter.

The brains were isolated from the decapitated heads, sliced into 3 or 5 coronal tissue slices as described below and then stained with hematoxylin and eosin to determine the extent of the ischemic area. Stained slices were photographed and subsequently imaged using a Macintosh Cadre 800 computer, equipped with an Image 1.47 software program for the assessment of the cross-sectional area of the ischemic lesion. These images and the calculated area of ischemic damage were stored in the program for later retrieval and data reduction. The significance of differences in mortality among the different treatment groups was determined using Chi-Square analysis.

The results obtained using different routes of administration and different isomeric forms of estrogen compounds are provided below.

The administration of an estrogen compound subcutaneously using Silastic® tubes or by controlled intravenous delivery, at 24 hours prior to the ischemic event, caused brain lesion size and mortality to be reduced.

Three coronal slices were made at 1, 5, and 7 mm posterior to the olfactory bulb. Only 35% of the control (sham treated) animals survived until the scheduled post-ischemic sacrifice time (Table 1). In contrast, 78%, and 84% of animals, treated 24 hours prior to MCAO with either 17β-estradiol in a Silastic® pellet (E2 implant) or with E2-CDS at 1 mg/kg administered by an intravenous injection survived until the scheduled post-ischemic sacrifice time at 6 hours, 1 day, and 1 week. Elevated levels of 17β-estradiol were detected in all samples at the time of sacrifice. The reduction in mortality in the estrogen compound pretreatment group was most notable at 1 day and 1 week after MCAO (Table 1). Furthermore, the reduced mortality in the estrogen compound treated rats was correlated with the reduction of ischemic area in animals that survived to the scheduled 1 day or 1 week post-ischemia sacrifice time (FIG. 1). Control (sham) rats had ischemic lesions that occupied 25.6±5.7% of the cross-sectional area of brain sections evaluated (FIG. 1). By contrast, rats treated with 17β-estradiol in Silastic® tubes or E2-CDS had ischemic lesions that occupied only 9.8±4.0 and 9.1±4.2%, respectively, of the brain area evaluated. The significance of differences among groups was determined by analysis of variance (ANOVA) and the Fischer's test was used for the post hoc comparison. Determination of areas under the curves were not done here as only three brain slices were taken.

Figure 2:
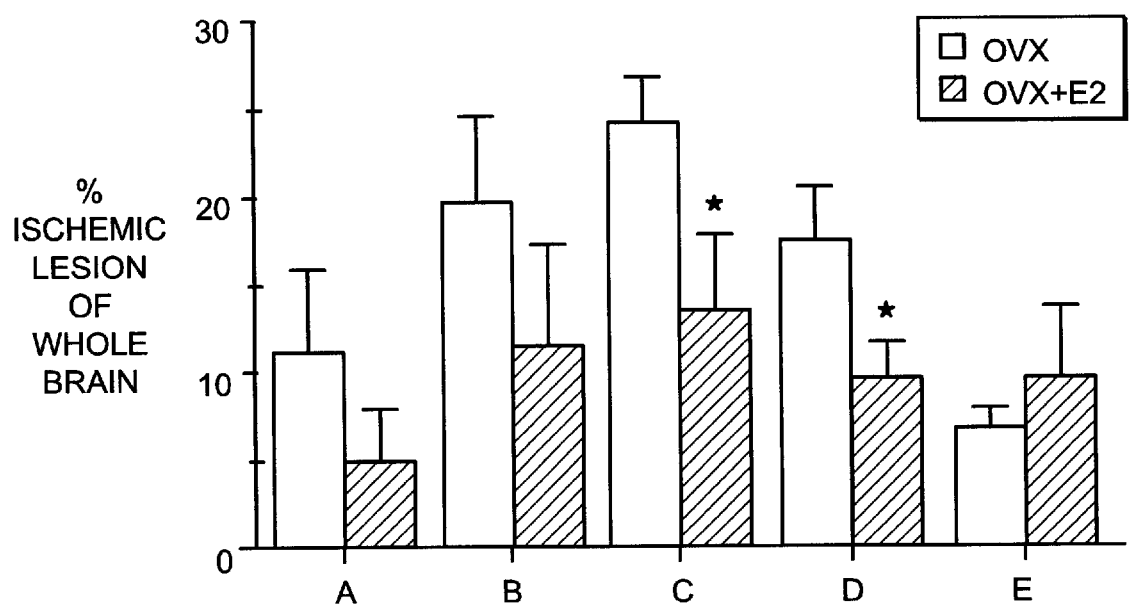
FIG. 2 is a bar graph that shows the effects of treatment of ovariectomized (OVX) rats with 17β-estradiol, at 2 hours prior to ischemia induced by MCAO, where the 17β-estradiol (10 μg/kg) is injected subcutaneously in an oil vehicle. Rats were decapitated 24 hours after the MCAO. Rat brains were dissected coronally as region A–E, 24 hours after MCAO. Values were given as the mean±SEM where n=8 for OVX+$E_2$ group and n=6 for OVX group(control). * p<0.05 vs. corresponding vehicle control groups.

The results shown in FIG. 2 illustrate the significant protective effect of estrogen compounds in tissue slices A–D in animals treated with subcutaneous injection of 17β-estradiol (10 μg/ml) two hours prior to an ischemic event.

Rats were ovariectomized, treated with a single dose of 17β-estradiol (10 μg/kg) by a sc injection, 14 days after the ovariectomy and two hours prior to the ischemic event as described above. This injection was sufficient to achieve a plasma concentration of 250 pg/ml at the time of occlusion. The animals were sacrificed at 24 hours and the brains extracted. Estrogen compound replacement of ovariectomized rats reduced by 46.3% and 44.1% (p<0.05) ischemic lesion size of the whole coronal section at region C and D, respectively (FIG. 2). These regions correspond to sections taken at 9 and 11 mm caudal to the olfactory bulb.

Figure 3:
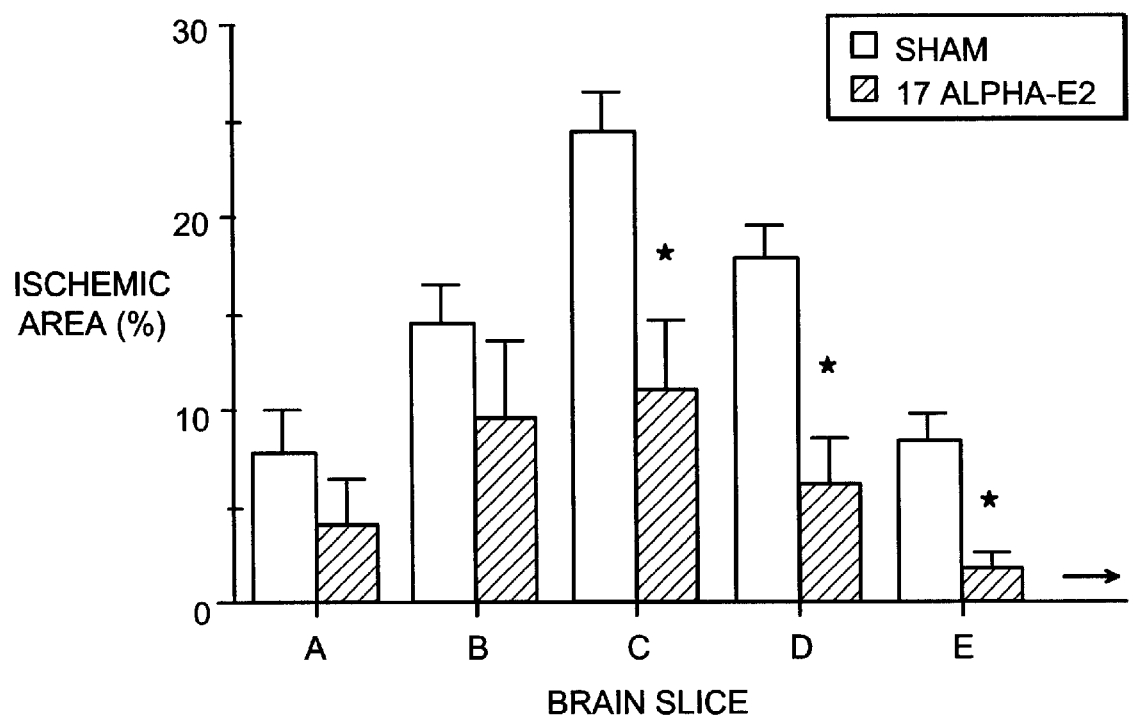
FIG. 3 is a bar graph that shows the effects of pretreatment of ovariectomized rats with 17α-estradiol, initiated 24 hours prior to ischemia induced by MCAO, where the 17α-estradiol is administered in a 5 mm Silastic® tube, and the negative control is a 5 mm Silastic® tube without estrogen (sham). Rats were decapitated 24 hours after the MCAO. Values are given as the mean±SEM for the percent ischemic area in 5 brain slices. A to E designate the distance caudal to the olfactory bulb A=5 mm, B=7 mm, C=9 mm, D=11 mm, and E=13 mm. *=$p<0.05$ vs. sham group for the equivalent brain slice; for sham n=10 and for 17α-estradiol groups, n=13.

The results shown in FIG. 3 illustrate the significant protective effect of 17α-estradiol in tissue slices A–E in animals treated with a sustained subcutaneous delivery of 17α-estradiol initiated 24 hours prior to the ischemic event.

Ovariectomized rats were treated with 5 mm Silastic® tubes containing 17α-estradiol at 24 hours prior to MCAO.

At 24 hours after the MCAO, the animals were sacrificed and the brains extracted. Five, 2 mm thick coronal sections were made at 5, 7, 9, 11, and 13 mm posterior of the olfactory bulb. The slices were then incubated for 30 minutes in a 2% solution of 2,3,5-triphenyltetrazolium (TTC) (Sigma Chemical Corp., St. Louis, Mo.) in physiological saline at 37° C. Sham-treated rats showed the expected ischemic lesion areas, with the maximum ischemic area (24.1±2.4%) occurring in slice C (9 mm posterior to the olfactory bulb) and smaller lesion areas occurring in more rostral and caudal slices (FIG. 3). The significance of differences between sham and steroid-treated groups, were thus determined and data from two groups were compared for each experiment. To determine the area under the lesion curve for a given treatment, the trapezoidal method was used. Areas calculated for each animal were grouped and the differences between groups were determined by the Student t test.

Animals pretreated with 17α-estradiol exhibited smaller ischemic areas compared with the sham treated animals in all slices evaluated (FIGS. 3, A–E). Specifically, slices C, D and E (sections taken at 7, 9, and 11 mm posterior to the olfactory bulb), ischemic area was reduced significantly by 55%, 66%, and 81%, respectively (FIG. 3). The area under the ischemic lesion curve for the sham-treated, and the 17α-estradiol groups was 8.1±0.8 and 3.7±1.3, respectively (Table 2).

Example 2.

Measurement of the Effect of Estrogen Compounds Administered After the Ischemic Event.

To test the extent to which estrogen treatment was effective after the onset of the occlusion, ovariectomized rats were treated iv with a sustained release of either E2-CDS or with a control (HPCD vehicle), the positive sample causing a brain tissue concentration of estrogen of 1000 pg estrogen per gram of brain tissue, 24 hours after administration. The estrogen compound was administered at 40 minutes and 90 minutes after the onset of the MCAO (FIGS. 4a and 4b, Table 2) and the animals sacrificed at 24 hours after the MCAO. Five 2 mm thick coronal sections were made at 5, 7, 9, 11, and 13 mm posterior of the olfactory bulb as described in Example 1.

Figure 4A:
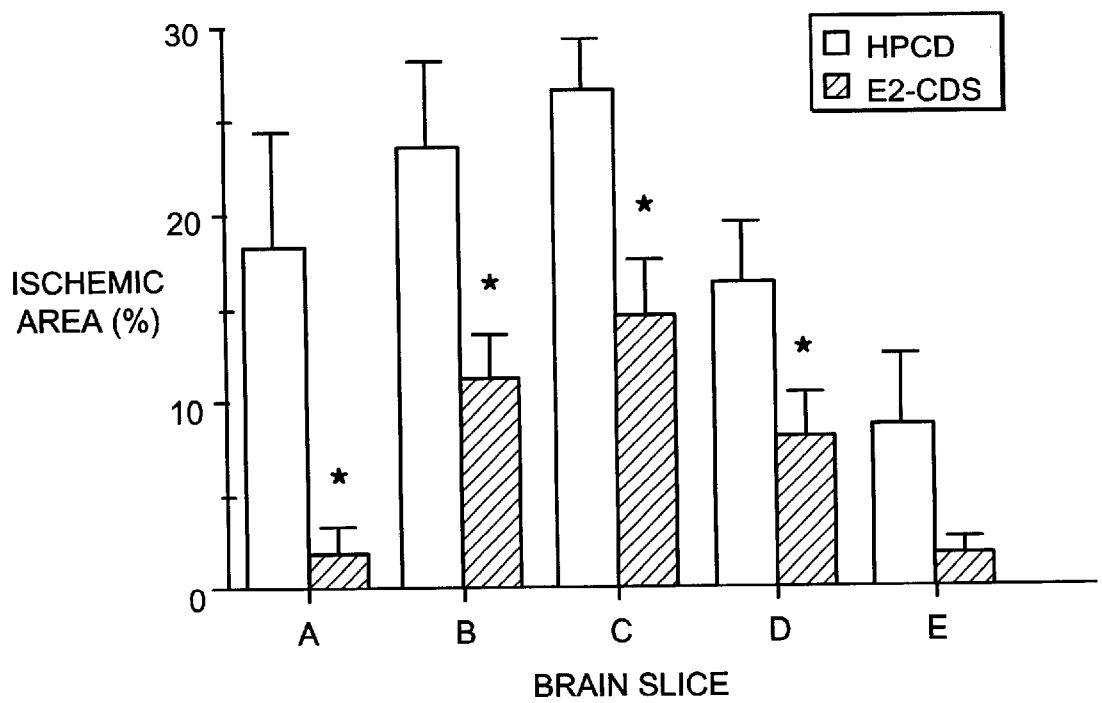
FIG. 4 is a bar graph that shows the effects of post-treatment of ovariectomized rats with 17β-estradiol or a hydroxypropyl cyclodextrin (HPCD) control at 40 minutes (a) and 90 minutes (b) post onset of MCAO. The 17β-estradiol was formulated in an estradiol chemical delivery system (E2-CDS) at a concentration of 1 mg/kg body weight and injected intravenously. Rats were decapitated 24 hours after the MCAO. Values are given as the mean±SEM for the percent ischemic area in 5 brain slices. A to E designate the distance caudal to the olfactory bulb A=5 mm, B=7 mm, C=9 mm, D=11 mm and E=13 mm. Where *=$p<0.05$ vs HPCD group for the same brain slice, N=9 for vehicle, and 13 for E2-CDS groups.

The results of post-treatment at 40 minutes are shown in FIG. 4a. The control rats (HPCD treated) had large ischemic areas in all slices sampled, with the maximum ischemic area of 25.6±2.7% observed in slice C. E2-CDS treatment reduced the ischemic area in all slices sampled (FIG. 4). The extent of reduction in ischemic area ranged from 90% in slice A (5 mm posterior of the olfactory bulb) to 45% in slice C (9 m posterior to the olfactory bulb; FIG. 4a). The integrated area under the ischemic lesion curve was 10.1±1.6 for the vehicle treated rats and 4.5±0.9 for the E2-CDS animals (Table 2).

Figure 4B:
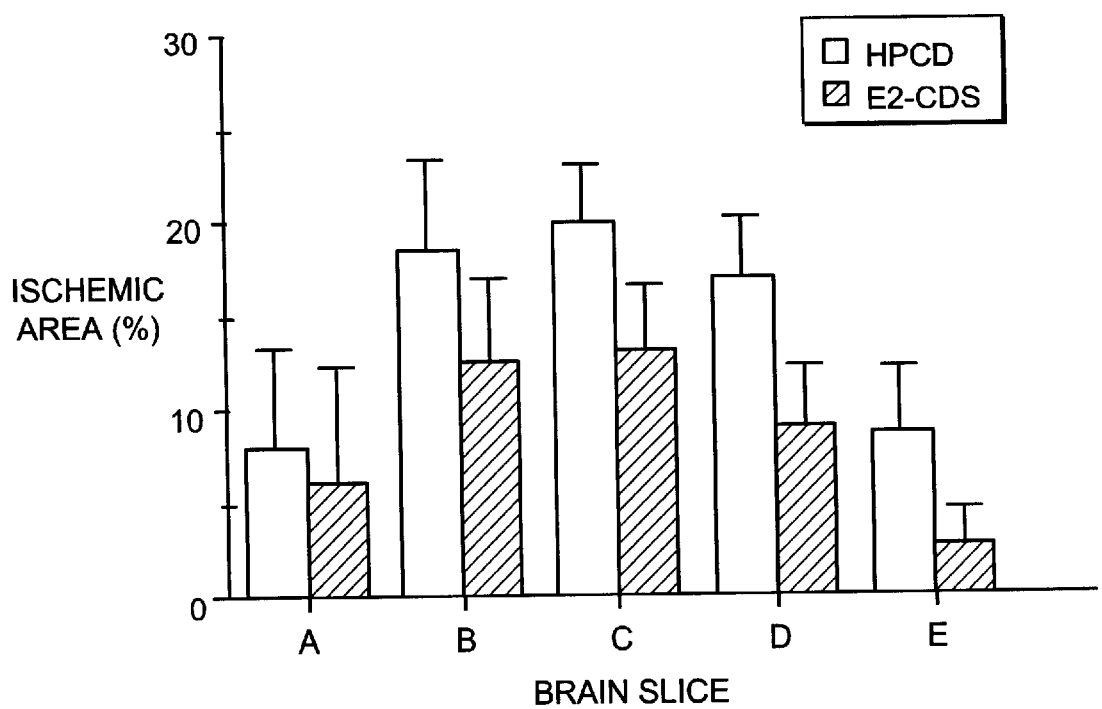

The results of post-treatment at 90 minutes of rats treated with E2-CDS or HPCD vehicle at 90 minutes after the onset of the occlusion are shown in FIG. 4b and Table 2. Again, HPCD treated animals showed a large lesion in all slices sampled, with the maximum ischemic area seen in slice C (20.5±3.1% of the slice area). Treatment with E2-CDS reduced the mean ischemic area in all slices examined, however, the differences were not statistically significant. An evaluation of the area under the ischemia curve for the two groups revealed that treatment with E2-CDS reduced the ischemic area by 37.1% from 8.2±1.7 (HPCD treated animals) to 5.2±1.7 (E2-CDS treated animals).

Example 3

Estrogen Compounds Protect Brain Capillary Endothelial Cells under Conditions Associated with Focal Ischemia Primary rat brain capillary endothelial cells (BCEC) cultures were prepared following the method of Goldstein, J. Neurochemistry vol. 25, 715–717, 1975, incorporated herein by reference.

Hypoglycemia experiments were undertaken. 17β-estradiol (2 nm) or control (ethanol vehicle) were added to BCEC cultures. The glucose concentration of the culture media was then adjusted from 20 mg % to 200 mg % by adding appropriate amount of D-(+)-glucose to the glucose-free media and monitored by Glucose and L-Lactate Analyzer (YSI model 2300 STAT plus, YSI, Inc., Yellow Springs, Ohio). The hypoglycemic cultures were maintained for 24 hours or 48 hours prior to staining with Trypan blue.

Anoxia environment was created by placing culture dishes containing BCEC with or without 2 mn 17β-estradiol in the Modular Incubator Chamber (Billups-Rothenberg, Inc., Delmar, Calif.). Nitrogen gas was influxed to replace the oxygen inside the chamber. The chamber was sealed and placed in the incubator for four hours for nonhypoglycemic cultures and 2 hours for hypoglycemic cultures.

Cell mortality was counted using Trypan blue staining method. Cell death percentage was calculated as dead cell/alive cell x100%.

Statistical treatment included two-way analysis of variance applied to determine the significance of the difference among the experimental groups. Kruskal-Wallis nonparametric analysis was used for data presented as percentage. The Mann-Whitney U tests were used when Kruskal-Wallis showed significance among groups. $P<0.05$ was considered significant.

Figure 5A:
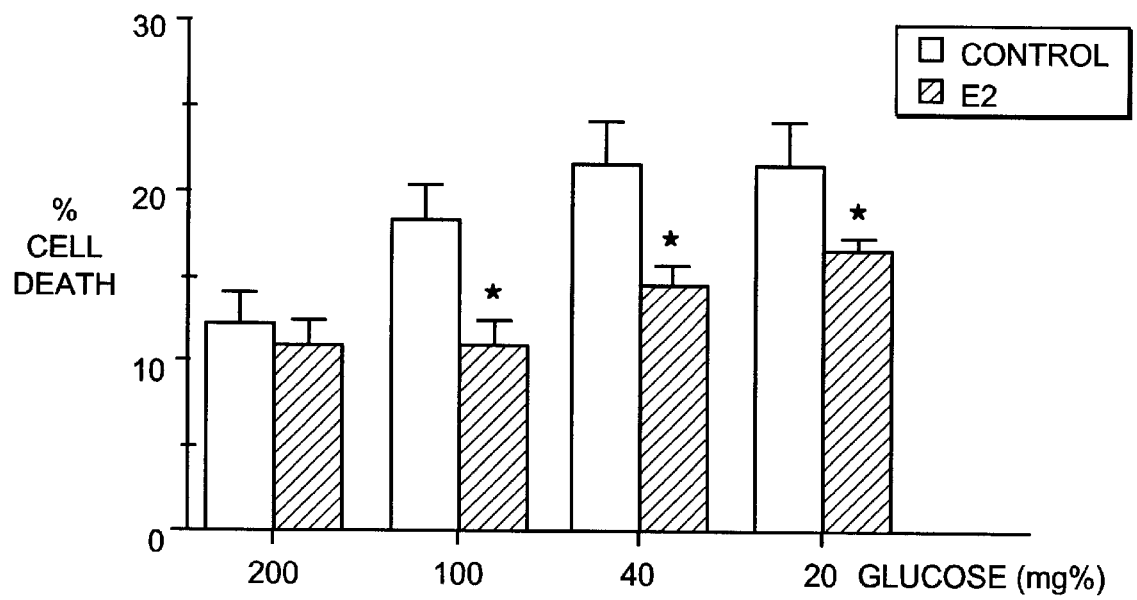
FIG. 5 is a bar graph that shows the effects of 17β-estradiol (2 nM) on brain capillary endothelial cell (BCEC) mortality following 24 hours of hypoglycemia. The control consists of the ethanol vehicle only. The glucose concentrations in the cell media were adjusted from 20 mg % to 200 mg % by adding appropriate amount of D-(+)-glucose to the glucose-free media. BCEC were incubated for 24 hours (a) and 48 hours (b). Trypan blue staining was used to distinguish live cells from dead cells. Two cell countings at two different hemacytometer squares were averaged. Mean±SEM are depicted (n=8–12). *$p<0.05$ vs. corresponding vehicle control.
Figure 5B:
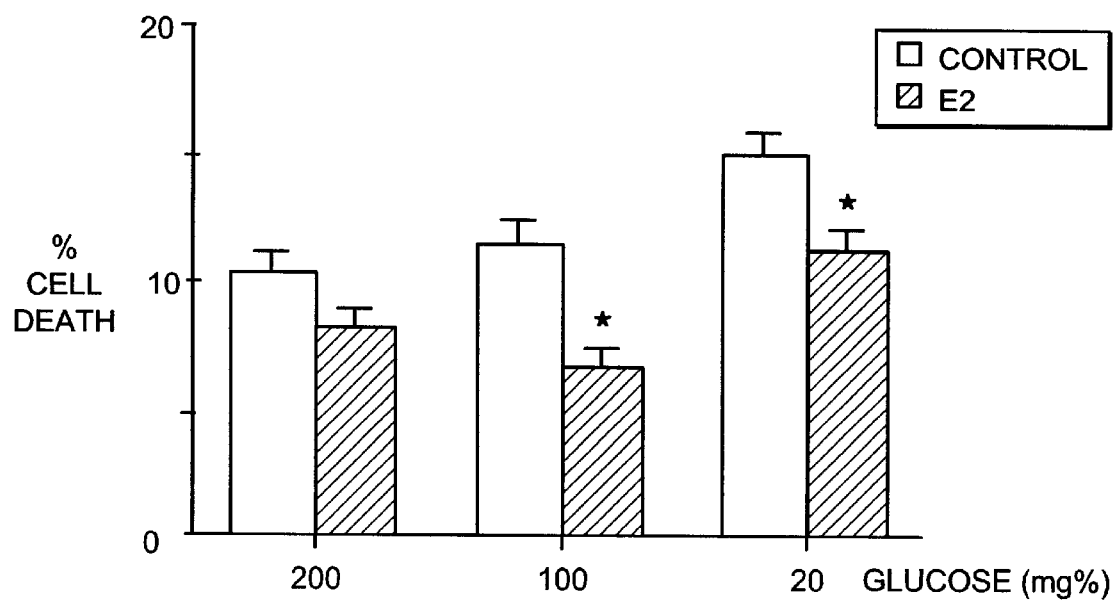

The results are shown in FIGS. 5a and 5b for cells deprived of glucose. The normal glucose concentration in the media is 200 mg % and there is little difference in % cell death between cultures with and without estrogen supplement. However, reduction in media glucose to 100 mg %, 40 mg %, and 20 mg % caused cell death, and 17β-estradiol saved cell loss by 35.9%, 28.4% and 23.% (p<0.05), respectively, compared with corresponding control groups. It was further noted that there were floating cells, which meant more dead cells, in the control groups than in the estradiol treated groups. Since these cells were excluded when counting cell mortality, the protective effects of estradiol may be underestimated. A similar beneficial effect was observed over a 24 hour and 48 hour hypoglycemic treatment (FIGS. 5a and 5b, respectively).

Anoxia had a more dramatic effect in cell viability as shown in FIG. 6 for cells in media containing 200 mg % glucose. Anoxia induced cell death as much as 48.8% and 39.8% in the control and E2 reduced cell death by 28.4% (p<0.05) at 1-hour and 18.4% (p<0.05) at 4-hour anoxic insults.

When cells were exposed to both hypoglycemia (100 mg % hypoglycemia) and anoxia conditions (2 hours), 17β-estradiol was effective in protecting cultured BCEC from the cumulative effect of both conditions (FIG. 7).

The in vitro assay is representative of events that follow ischemia such as that induced by MCAO where oxygen and glucose supplies to the blood-brain barrier endothelial cells are reduced.

Example 4

Comparison of Post-Treatment at 0.5, 1, 2, 3 and 4 Hours

Figure 8:
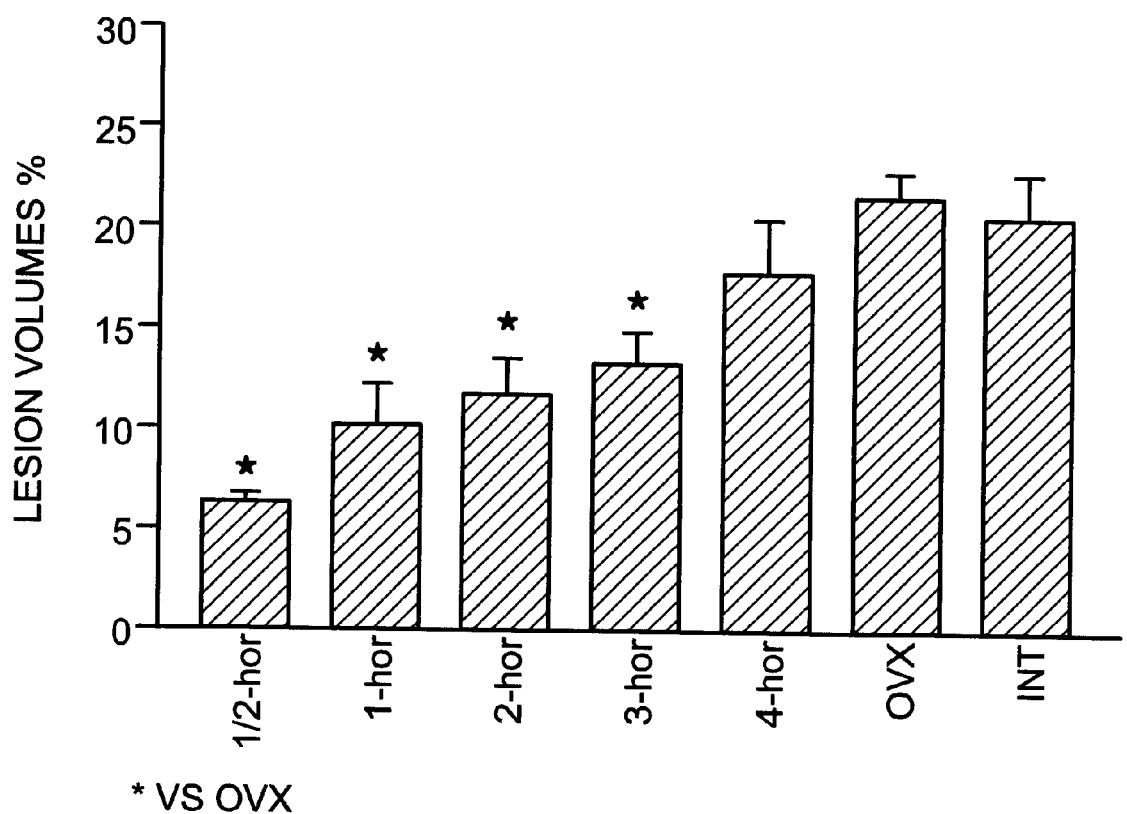
FIG. 8 is a bar graph that shows the effects of post-treatment of ovariectomized (OVX) rats with 17β-estradiol at 0.5, 1, 2, 3, and 4 hours following ischemia induced by MCAO. The estrogen compound was administered by a combination of an intravenous preparation (100 µg/kg) of HPCD-complexed 17β-estradiol and Silastic® pellet at the times post-occlusion indicated. Ovariectomized, non-treated animals (OVX) and non-ovariectomized, non-treated animals (INT) were used as controls (n=12 and n=6, respectively). At 48 hours following MCAO, ischemic lesion volume was determined using 2,3,5-triphenyl tetrazolium (TTC) staining.

Ovariectomized rats were treated with both an intravenous injection (100 μg/kg) of HPCD-complexed 17β-estradiol and a 17β-estradiol containing Silastic® pellet at the times indicated after the onset of occlusion (FIG. 8). HPCD and HPCD-encapsulated 17β-estradiol were purchased from Sigma (St. Louis, Mo.). Ovariectomized, non-treated animals (OVX) and non-ovariectomized, non-treated animals (INT) were used as controls (n=12 and n=6, respectively).

At 48 hours following MCAO, animals were sacrificed and ischemic lesion volume was determined by obtaining brain sections as previously described, and staining with TTC. FIG. 8 shows that significant protection was observed when drugs were administered 0.5, 1, 2 or 3 hours post-occlusion.

Example 5

Intravenous Delivery of a Sodium Sulfated Estrogen Compound

Sodium sulfate 17β-estradiol, rather than the free steroid, was used to increase the solubility of an estrogen compound in an aqueous medium. The sodium sulfate 17β-estradiol solution was prepared fresh on a daily basis in a vehicle that contained, in one embodiment, 2% benzyl alcohol by volume and 200 mg lactose per ml double-distilled water. (In different embodiments, the presence of and quantity of each of the alcohol and sugar can be varied, and in others those components can be omitted).

Animals were ovariectomized at least two weeks prior to use in the Example, and were cannulated one day prior to intravenous administration of the drug. Blood samples (one ml) were taken via the cannula, were centrifuged immediately, and erythrocytes were resuspended in heparinized saline (40 IU/ml) and returned to the animal following the subsequent blood sample. 17β-estradiol was measured in plasma samples using a commercially supplied radioimmunoassay kit, which measure free 17β-estradiol and does not cross react with the sulfated form of the steroid.

FIG. 9 shows the mean plus and minus the SEM for 8 animals (through the 4 hour blood sampling). When SEM is not depicted, the data at that point had an SEM smaller than the area covered by the symbol used to depict the mean. FIG. 9 shows that estrogen compounds delivered intravenously as the sodium sulfated form was effective in rapid achievement of a high blood level (approximately 2,500 pg/ml) of the compound within 5 min.

TABLE 1

Effects of Pretreatment with 17 β-Estradiol or an Estradiol-Chemical Delivery System (E2-CDS) on Mortality Following Middle Cerebral Artery Occlusion

| Treatment | Time of Planned Sacrifice | Number of Animals Tested | Number of Animals Alive | Number of Animals Dead | % Survival |
|---|---|---|---|---|---|
| Sham | 6 hrs | 12 | 5 | 7 | 42 |
|  | 1 Day | 18 | 6 | 12 | 33 |
|  | 1 Week | 5 | 1 | 4 | 20 |
|  | Total | 35 | 12 | 23 | 35 |
| E2 Implant | 6 hrs | 6 | 3 | 3 | 50 |
|  | 1 Day | 8 | 8 | 0 | 100* |
|  | 1 Week | 4 | 3 | 1 | 75* |
|  | Total | 18 | 14 | 4 | 78* |
| E2-CDS | 6 hrs | 7 | 5 | 2 | 71 |
|  | 1 Day | 8 | 7 | 1 | 88* |
|  | 1 Week | 4 | 4 | 0 | 100 |
|  | Total | 19 | 16 | 3 | 84* |

*$p < 0.05$ versus sham control group at each of the time points, as determined by Chi Squares analysis.

TABLE 2

Effects of Estrogens on the Area Under the Ischemic Lesion Curve in Ovariectomized Rats

| Steroid | Treatment | Area Under Curve |
|---|---|---|
| Sham | 24 hour pretreatment | 8.1 ± 0.8 |
| 17α-estradiol | 24 hour pretreatment | 3.7 ± 1.3* |
| HPCD Vehicle | 40 min posttreatment | 10.1 ± 1.6 |
| E2-CDS | 40 min posttreatment | 4.5 ± 0.9* |
| HPCD Vehicle | 90 min posttreatment | 8.2 ± 1.7 |
| E2-CDS | 90 min posttreatment | 5.21 ± 1.7 |

*$p < 0.02$ versus sham control by Students t test

We claim:

1. An improved method of treating ischemia in a subject, comprising:
   providing desulfated estrogen in the blood plasma of the subject by administering to the subject intravenously, at least one dose of a preparation containing a sulfated salt of an estrogen compound at a time that is effectively proximate to the ischemic event.

2. A method according to claim 1, wherein the proximate time precedes the ischemic event.

3. A method according to claim 1, wherein the proximate time follows the ischemic event.

4. A method according to claim 3, wherein the proximate time is within 12 hours of the ischemic event.

5. A method according to claim 1, wherein the ischemic event is selected from the group consisting of a cerebrovascular disease, subarachnoid hemorrhage, myocardial infarct, surgery and trauma.

6. A method according to claim 1, wherein the ischemic event is a stroke.

7. A method according to claim 1, wherein the estrogen compound is selected from the group consisting of alpha isomers and beta isomers of estrogen.

8. A method according to claim 1, wherein the ischemic event is a myocardial infarct.

9. A method according to claim 1, wherein the estrogen compound is administered at an effective dose, wherein the effective dose provides a plasma concentration in the subject in the range of 10–500 pg/ml.

10. A method for conferring protection on a population of cells associated with an ischemic focus, in a subject following an ischemic event, comprising:
   (a) selecting a sodium sulfate form of an estrogen compound;
   (b) formulating the sodium sulfate of the estrogen compound in an intravenous delivery vehicle; and
   (c) administering the formulation to a subject intravenously to provide desulfated estrogen in the blood and reducing the adverse effects of the ischemic event.

11. A method according to claim 10, wherein (c) further comprises administering an effective amount of the compound over a course that includes at least one dose within a time that is effectively proximate to the ischemic event, so as to confer protection on the population of cells.

12. A method for protecting cells from degeneration in a subject, comprising:
   (a) providing an effective dose of a sodium sulfate form of an estrogen compound and administering the sulfated estrogen intravenously to provide desulfated estrogen in the blood within 5 minutes after administration; and
   (b) protecting cells from degeneration otherwise occurring in the absence of the estrogen compound.

13. A method of treating stroke in a subject, comprising:
(a) providing an effective dose of a sodium sulfate form of an estrogen compound in a delivery vehicle; and
(b) administering the formulation to the subject intravenously so as to reduce the adverse effects of the stroke.

14. A method of treating an ischemic event in a subject, comprising:
(a) providing a sodium sulfate form of an estrogen compound in an intravenous delivery vehicle; and
(b) administering an effective amount of the compound over a course that includes a first dose within a time that is effectively proximate to the ischemic event, so as to confer protection on the population of cells.

15. A method according to claim 14, wherein the estrogen compound is an alpha isomer of estrogen.

16. A method according to claim 14, wherein step (b) further comprises administering the first dose of the estrogen compound within 12 hours of the ischemic event.

17. A method according to claim 14, wherein step (b) further comprises administering an estrogen compound having insubstantial sex related activity.

18. A method according to claim 14, wherein the ischemic event is selected from the group consisting of a cerebrovascular disease, subarachnoid hemorrhage, myocardial infarct, surgery and trauma.

19. A method according to claim 14, wherein the ischemic event is a myocardial infarct.

20. A pharmaceutical formulation comprising: a sodium sulfate form of an estrogen compound in a delivery vehicle suitable for intravenous administration, the formulation providing a peak plasma concentration of desulfated estrogen within 5 minutes after intravenous administration.

21. A method of providing desulfated estrogen in the blood within 5 minutes of administration, comprising:
(a) formulating a sulfated form of an estrogen in an aqueous vehicle; and
(b) administering the sulfated form of the estrogen intravenously.

22. A method according to claim 10 wherein the cells are neurons.

23. A method according to claim 10 wherein the cells are endothelial cells.

* * * * *

UNITED STATES PATENT AND TRADEMARK OFFICE
Certificate

Patent No. 6,326,365 B1            Patented: December 4, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: James W. Simpkins, Gainsville, FL; Katherone Gordon, Winchester, Wellesley, MA; and Robert J. Leonard, Wellesley, MA.

Signed and Sealed this Third Day of February 2004.

*FREDERICK KRASS*
*Supervisory Patent Examiner*
Art Unit 1614